US011105761B2

(12) United States Patent
Reuel et al.

(10) Patent No.: US 11,105,761 B2
(45) Date of Patent: Aug. 31, 2021

(54) RESONANT SENSORS FOR WIRELESS MONITORING OF CELL CONCENTRATION

(71) Applicant: Iowa State University Research Foundation, Inc., Ames, IA (US)

(72) Inventors: Nigel Forest Reuel, Ames, IA (US); Adam Russell Carr, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 16/793,617

(22) Filed: Feb. 18, 2020

(65) Prior Publication Data

US 2020/0264122 A1 Aug. 20, 2020

Related U.S. Application Data

(60) Provisional application No. 62/807,076, filed on Feb. 18, 2019.

(51) Int. Cl.
*G01N 27/22* (2006.01)

(52) U.S. Cl.
CPC ......... *G01N 27/226* (2013.01); *G01N 27/221* (2013.01)

(58) Field of Classification Search
CPC ............... G01N 27/226; G01N 27/221; G01N 2015/0065; G01N 15/0656; G01N 2015/0693; G01N 15/06; C12M 41/36
See application file for complete search history.

(56) References Cited

U.S. PATENT DOCUMENTS 5,715,337 A * 2/1998 Spitzer ................ G02B 27/017
359/223.1
7,775,083 B2 8/2010 Potyrailo et al.
(Continued)

FOREIGN PATENT DOCUMENTS

WO WO-2005/085818 A2 9/2005
WO WO-2013/057630 A1 4/2013
(Continued)

OTHER PUBLICATIONS

"International Application Serial No. PCT/US2020/018640, International Search Report dated Aug. 28, 2020", 4 pgs.
(Continued)

*Primary Examiner* — Christopher P McAndrew
*Assistant Examiner* — Zannatul Ferdous
(74) *Attorney, Agent, or Firm* — Schwegman Lundberg & Woessner, P.A.

(57) ABSTRACT

Various embodiments relate to a resonator system that can be used to monitor proteins, cells, or small molecules in a container. A resonant sensor, embedded in or on the container, can have an inductive element and a capacitive element, where the container and resonant sensor are structured such that, when a concentration of the proteins, cells, or small molecules in the container changes, dielectric permittivity and conductivity of the proteins, cells, or small molecules contributes to capacitance of the resonant sensor to affect a resonant frequency shift of the resonant sensor. Interrogating the resonant sensor can be conducted wirelessly along with wirelessly transmitting data collected from the interrogation. Additional apparatus, systems, and methods are disclosed.

22 Claims, 11 Drawing Sheets

(56) References Cited

U.S. PATENT DOCUMENTS

| | | | |
|---|---|---|---|
| 9,274,071 | B2 | 3/2016 | Potyrailo et al. |
| 2012/0073633 | A1* | 3/2012 | Fujdala ............ H01L 21/02491 136/252 |
| 2012/0138460 | A1* | 6/2012 | Baghbani-Parizi ........................ B01L 3/502715 204/450 |
| 2013/0175862 | A1* | 7/2013 | Kelly ................... H02J 1/14 307/24 |
| 2013/0228473 | A1* | 9/2013 | Wilsey ................. C12Q 1/006 205/777.5 |
| 2014/0275944 | A1* | 9/2014 | Semenov ............... A61B 5/053 600/407 |
| 2015/0247820 | A1* | 9/2015 | Davalos ................. B03C 5/026 204/605 |
| 2016/0161425 | A1* | 6/2016 | Berezin ................. G01N 22/00 324/638 |
| 2016/0187277 | A1* | 6/2016 | Potyrailo ........... G01N 33/2888 324/633 |
| 2016/0244712 | A1* | 8/2016 | Potyrailo ............ G01N 27/026 |
| 2020/0253504 | A1* | 8/2020 | Shen ................... A61B 5/0538 |

FOREIGN PATENT DOCUMENTS

| | | |
|---|---|---|
| WO | WO-2015/101528 A1 | 7/2015 |
| WO | WO-2020/172163 A2 | 8/2020 |
| WO | WO-2020/172163 A3 | 10/2020 |

OTHER PUBLICATIONS

"International Application Serial No. PCT/US2020/018640, Written Opinion dated Aug. 28, 2020", 5 pgs.

Ebersole, Richard C., et al., "Piezoelectric Cell Growth Sensor", *Bio/Technology*, vol. 9, (May 1991), 450-454.

Konakovsky, Viktor, et al., "Universal Capacitance Model for Real-Time Biomass in Cell Culture", *Sensors*, 15(9), (2015), 22128-22150.

Ong, Keat G., et al., "Remote Query Resonant-Circuit Sensors for Monitoring of Bacteria Growth: Application to Food Quality Control", *Sensors*, 2(6), (2002), 219-232.

Wong, Jason, "Implementation of Capacitance Probes for Continuous Viable Cell Density Measurements for 2K Manufacturing Fed-Batch Processes at Biogen Idec", [online]. *IFPAC*, Retrieved from the Interent: <URL: http://www.infoscience.com/JPAC/ManScDB/JPACDBEntries/1394130144.pdf, (Jan. 24, 2014), 22 pgs.

Potyrailo, Radislav A., et al., "Label-free independent quantitation of viable and non-viable cells using a multivariable multi-resonant sensor", Bioelectrochemistry 125, (2019), 97-104.

* cited by examiner

RESONANT SENSORS FOR WIRELESS MONITORING OF CELL CONCENTRATION

PRIORITY APPLICATION

This application claims priority under 35 U.S.C. 119(e) from U.S. Provisional Application Ser. No. 62/807,076, filed on 18 Feb. 2019, which application is incorporated herein by reference in its entirety.

FIELD OF THE INVENTION

The invention relates generally to monitoring technologies, in particular, monitoring associated with biomanufacturing of proteins, cells, or small molecules.

BACKGROUND

In biomanufacturing of proteins, cells, or small molecules, measurements of concentrations of such objects are conducted. However, current routine measurements use sampling that can cause issues with respect to contamination.

BRIEF DESCRIPTION OF THE FIGURES

The drawings illustrate generally, by way of example, but not by way of limitation, various embodiments discussed in the present document.

DETAILED DESCRIPTION

Figure 1:
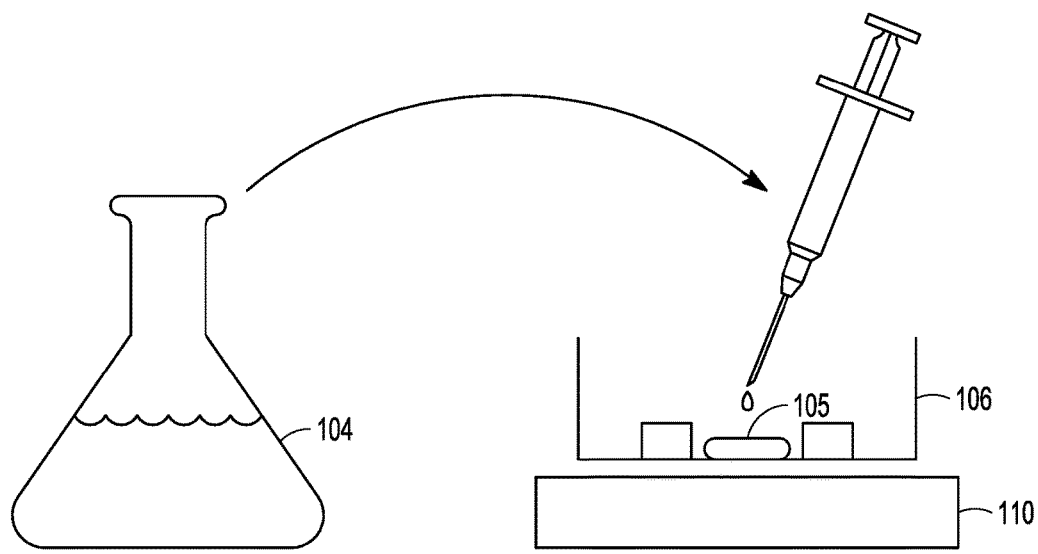
FIG. 1 is a test setup where a culture growth was sampled and placed on a resonator surface to determine a resonant sensor response, in accordance with various embodiments.

The following detailed description refers to the accompanying drawings that show, by way of illustration, various embodiments of the invention. These embodiments are described in sufficient detail to enable those of ordinary skill in the art to practice these and other embodiments. Other embodiments may be utilized, and structural, logical mechanical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, a mechanism is provided to measure cell concentration, on-line, in real time for biomanufacturing of proteins, cells, or small molecules. Current routine measurements, for example optical density (OD) measurements at 600 nm, use sampling that can cause issues of contamination. The mechanism as taught here can allow measurements of cell concentration to be made without breaking sterile conditions.

Resonant sensors can wirelessly transduce changes to the inductance, capacitance, and/or resistance of their circuit via modulation of their scattering parameters. These scattering parameters can be interrogated using a two loop vector network analyzer (VNA). In various embodiments, resonant sensors can be embedded on the surfaces of glass or plastic culture ware and can monitor cell concentration wirelessly. It has been shown previously that the local capacitance of the media increases as the number of cells in the media grow. See, for example, Konakovsky, V., Yagtu, A. C., Clemens, C., Muller, M. M., Berger. M., Schlatter, S., & Herwig, C. (2015). Universal Capacitance Model for Real-Time Biomass in Cell Culture; Sensors (Basel, Switzerland), 15(9), 22128-50, which is incorporated by reference herein in its entirety. The governing equation for resonant frequency of an LC resonator is $$f = 1/(2\pi\sqrt{(LC)})$$

where f is the frequency, L is the inductance of the resonator, and C is the capacitance of the resonator. Thus, as the cells grow, one would expect the resonant frequency of the LC circuit or resonator to decrease, if it is being influenced by the cell growth, through an increase in circuit capacitance. The resonator geometry can be optimized such that the effect of cell concentration on resonant frequency is increased.

The component arrangements and methods as taught herein can use an LC resonator in a novel manner to generate measurements of cell concentration. There are quite a few studies on measuring capacitance of a cell culture to determine the OD. Typically, these studies were performed with an inserted probe. Another study also included measurement with a wired LC resonator, in which the system could not be placed in an incubator. Furthermore, a previous study of an LC resonator test measured the permittivity of the fluid with a wired impedance analyzer. In contrast, the approach as taught herein allows a measurement structure to be placed in an incubator, where data collection can be conducted wirelessly from outside the incubator. In various embodiments, as taught herein, methods that include determination of resonant frequency can be used.

FIG. 1 shows a test setup in which 1 ml of *E. coli* culture growth was sampled every 15 minutes, measured for OD, and placed on a resonator surface to determine the sensor response. This setup provided an experimental validation. The experimental validation was a first proof of concept test that was performed by growing a 1 L volume of *E. Coli* from an overnight culture in a 2.5 L shake flask 104 and sampling 1 ml from the flask every 15 minutes and testing it for OD, using absorbance at 600 nm, as well as the resonant frequency on an inverted resonator 105, which can be made from etched Pyralux, as represented in FIG. 1. The resonator 105 in container 106 was interrogated by a two loop coil, sweeping 1-100 MHz range of frequencies using a vector network analyzer 110, located outside container 106, and the amplitude and phase of the scattering parameters was observed. The resonant frequency was identified from the S21 parameter and plotted vs. the measured OD of the sample. As shown in FIG. 1, vector network analyzer 110 can be used to wirelessly interrogate resonator 105 from outside container 106, which can avoid introducing contamination elements into container 106.

Figure 2:
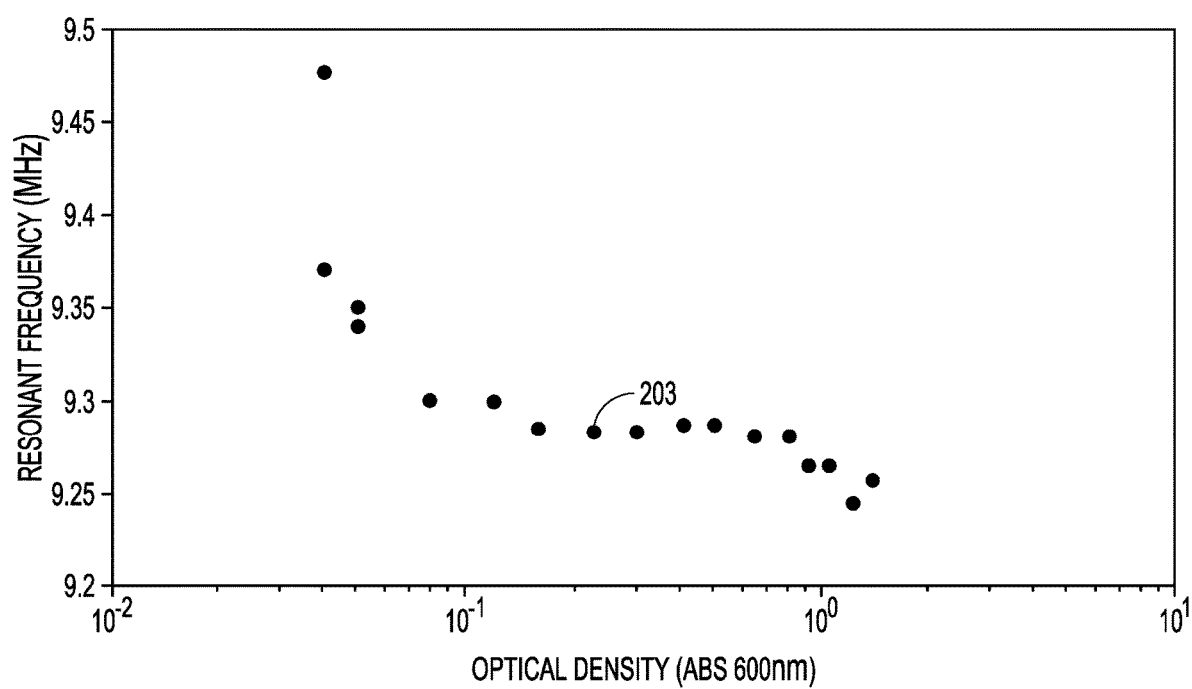
FIG. 2 is a curve of a plot of resonant frequency response versus optical density readings from a shake culture flask, sampled at intervals, in accordance with various embodiments.

FIG. 2 is a curve 203 of a plot of resonant frequency response vs. optical density readings from the shake culture flask 104 of FIG. 1, sampled at 15 minute intervals. As expected, curve 203 shows that the resonant frequency decreases as the cell concentration increases, exhibited by the increase in optical density. Of special interest, it appears that the resonant frequency shift is most pronounced at low cell concentrations. The sampled data also indicates to a very common problem of sensors that are not "on-line," that is not integrated in the system, which problem deals with there being quite a bit of operator error introduced by periodic sampling. This problem can be overcome with embedding the sensor in or on the culture flask directly.

Figure 3:
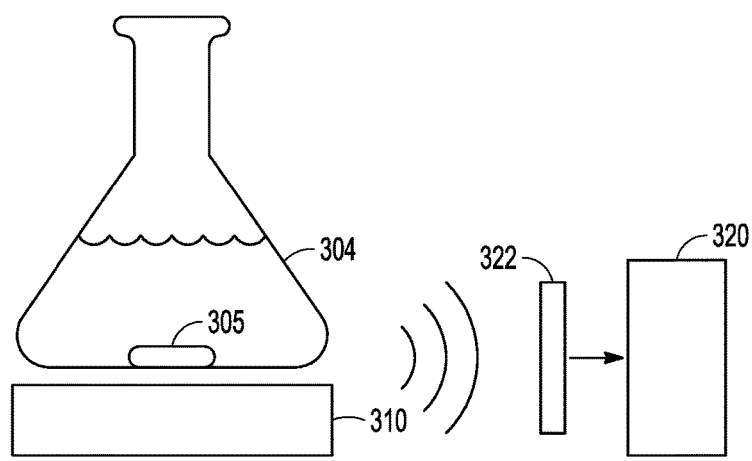
FIG. 3 illustrates a resonant sensor embedded in the bottom of the glass culture flask, in accordance with various embodiments.

FIG. 3 illustrates a resonant sensor 305 embedded in the bottom of the glass culture flask 304. This arrangement of resonant sensor 305 and glass culture flask 304 is incubated on a portable VNA 310, which transmits scattering parameter data to a computer 320, which can be a local computer. Computer 320 can be realized by a set of one or more processors, associated memory devices, and appropriate interfaces. Portable VNA 310 can be arranged to wirelessly receive signals from resonant sensor 305 to collect data reflecting resonant frequency of the resonant sensor 305 over time. In such an interrogation, the amount of signal power (dB) transmitted and absorbed through the resonator sensor 305 can be measured using VNA 310. Portable VNA 310 is located outside flask 304. The data can be provided to computer 320 via a communication interface 322. In an embodiment, the data can be provided to computer 320 via a communication interface 322, where the communication interface 322 can transmit, over a network, the scattering parameter data to computer 320 situated as a remote computer. The setup of FIG. 3 was used to provide a next proof of concept, in which the resonator sensor 305 was embedded in the bottom of the glass culture flask 305.

Figure 4:
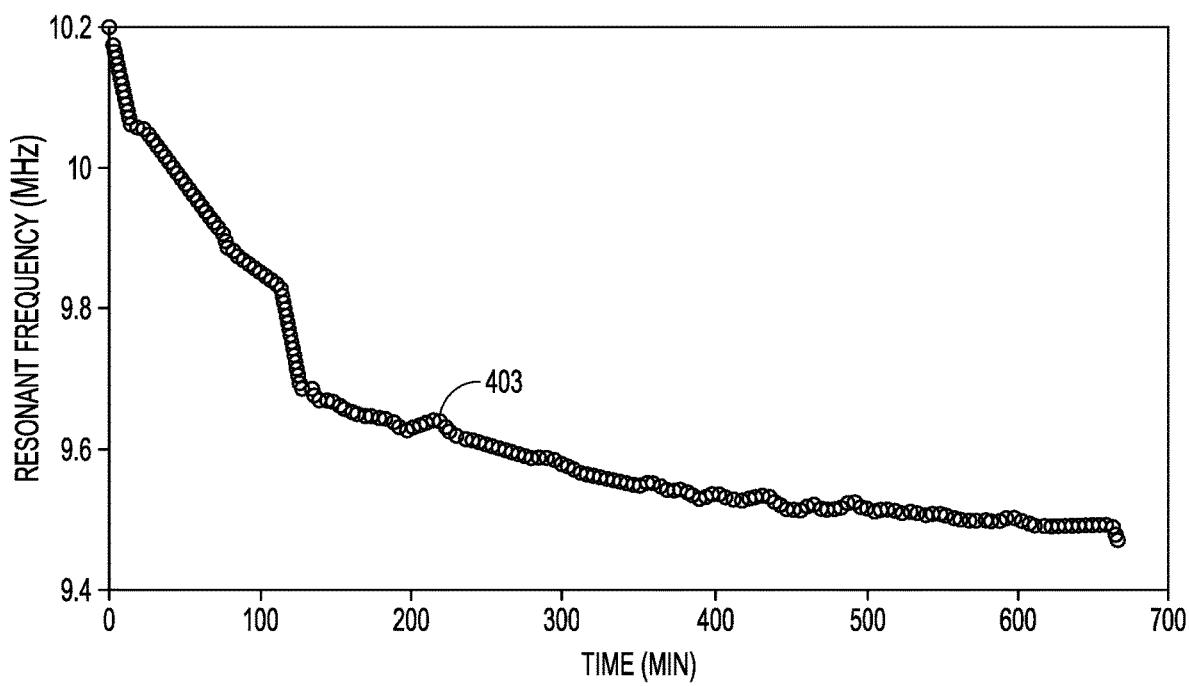
FIG. 4 is a curve of a resonant sensor response sampled in real time from a culture growing in the glass culture flask of FIG. 3, in accordance with various embodiments.

A copper resonator side down was epoxied on flask 304, leaving a thin, polyimide exposed to media and cells in the flask 304. *E. coli* cells were inoculated from an overnight growth of 30 μl in 300 ml total volume, and the resonant sensor 305 was interrogated every minute from the portable vector network analyzer 310 outside flask 304, where the portable vector network analyzer 310 transmitted its data via Bluetooth to computer 320. Other protocols can be used. The resonant frequencies were then determined for each data point and smoothed with a 10 minute averaging window. Again, the sensor response showed a decrease in resonant frequency as a function of cell growth as shown in FIG. 4. FIG. 4 is a curve 403 of a resonant sensor response sampled in real time from an *E. coli* culture growing in the glass culture flask 304 of FIG. 3, as discussed above.

Figure 5:
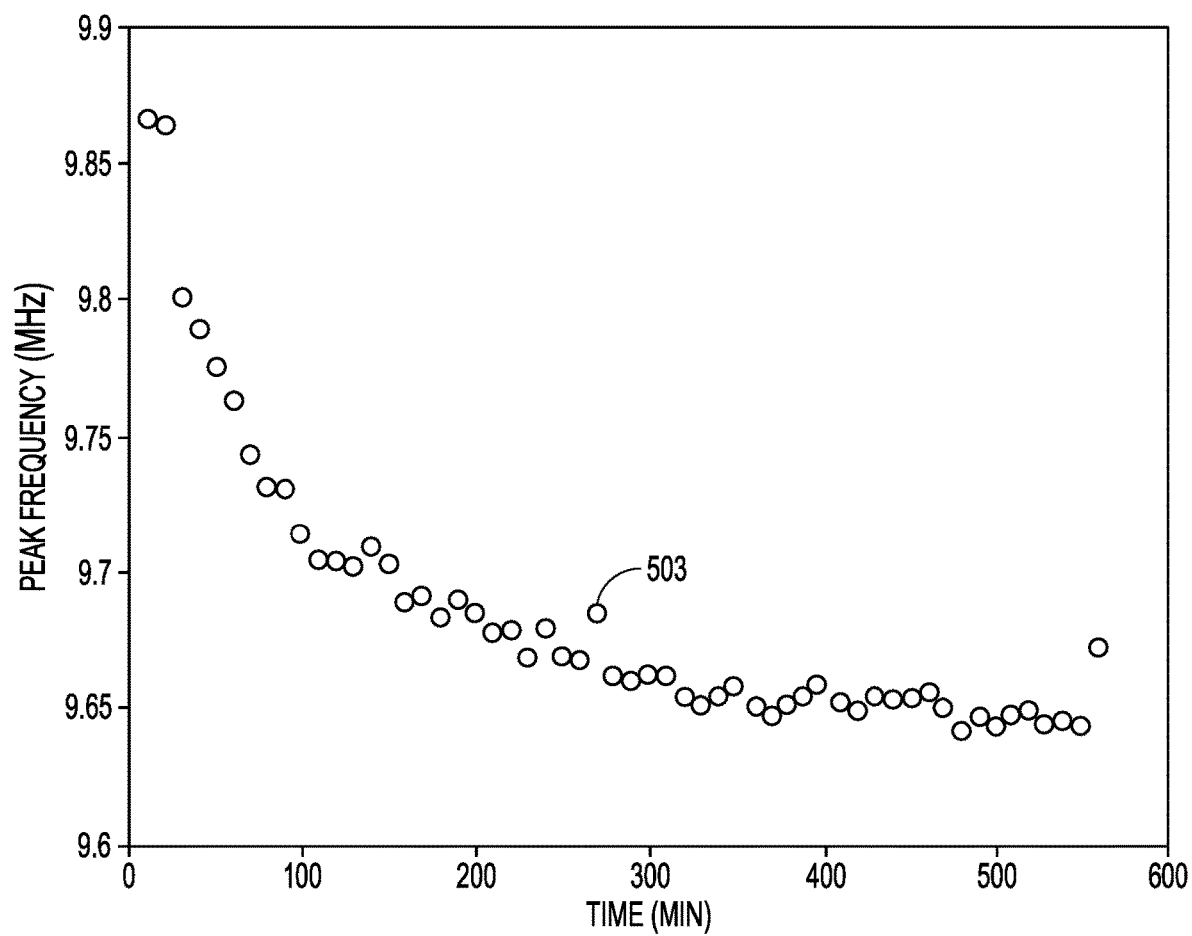
FIG. 5 shows a curve of a plot of resonant frequency of a culture in a shake flask arrangement, wirelessly measured, in accordance with various embodiments.

As a third data set, a portable reader was again used in a shake incubator arrangement similar to FIG. 3 and data was collected wirelessly. This time, OD data was also gathered with traditional absorbance at 600 nm measurement. Again, the decrease in resonant frequency with time was observed as shown in FIG. 5. FIG. 5 shows a curve 503 of a plot of resonant frequency of a *E. coli* culture in a shake flask arrangement, wirelessly measured from incubator.

Figure 6B:
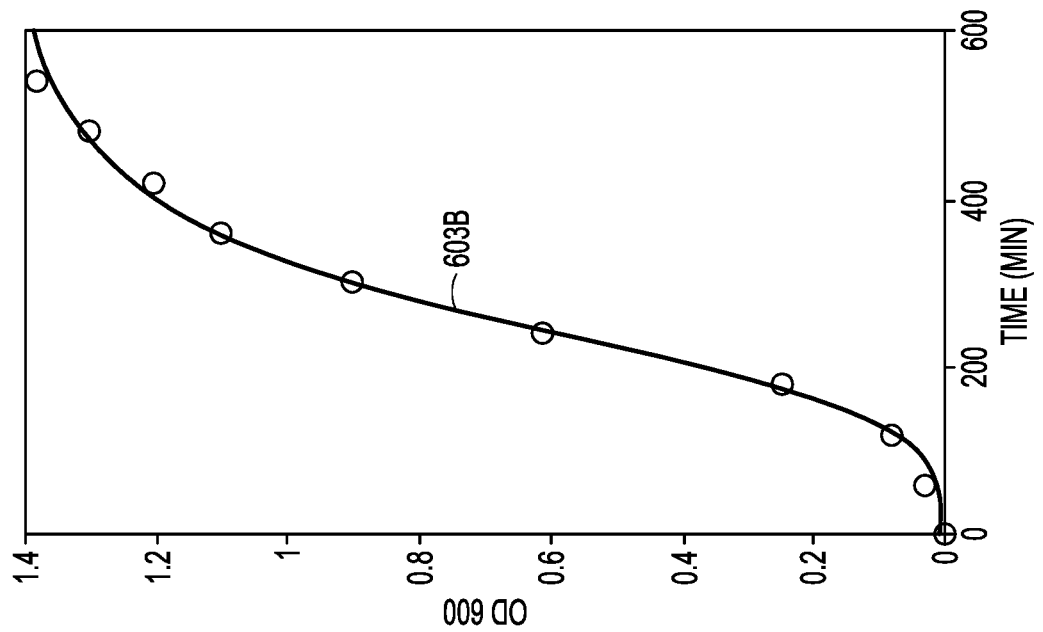
FIG. 6B shows optical density measured at 600 nm plotted as a function of time, in accordance with various embodiments.
Figure 6A:
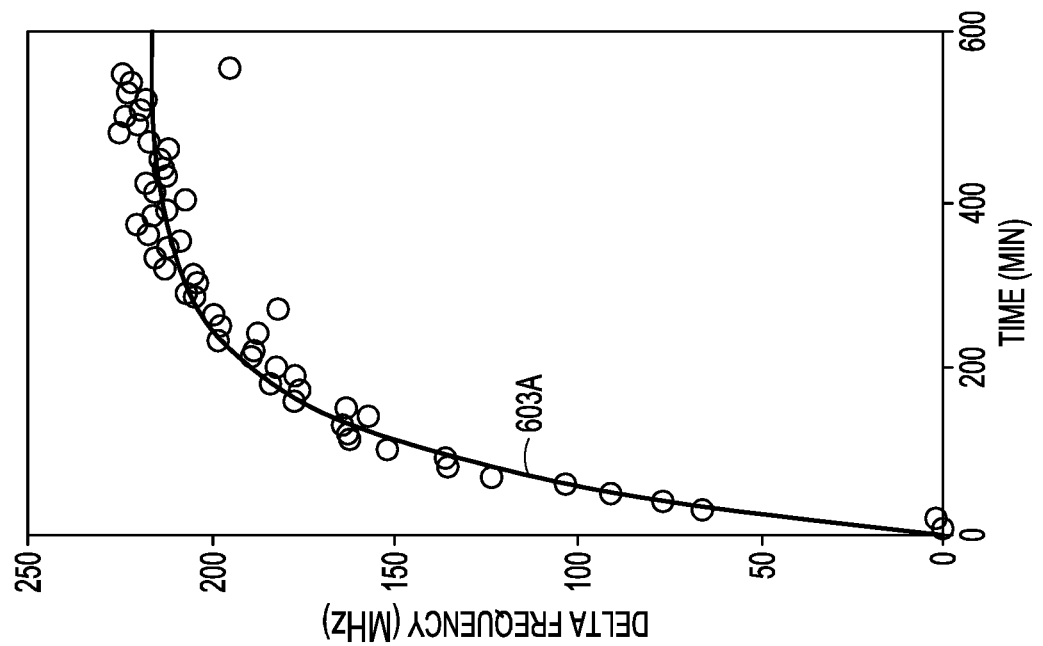
FIG. 6A shows data from FIG. 5 plotted as change in frequency versus time, in accordance with various embodiments.
Figure 7:
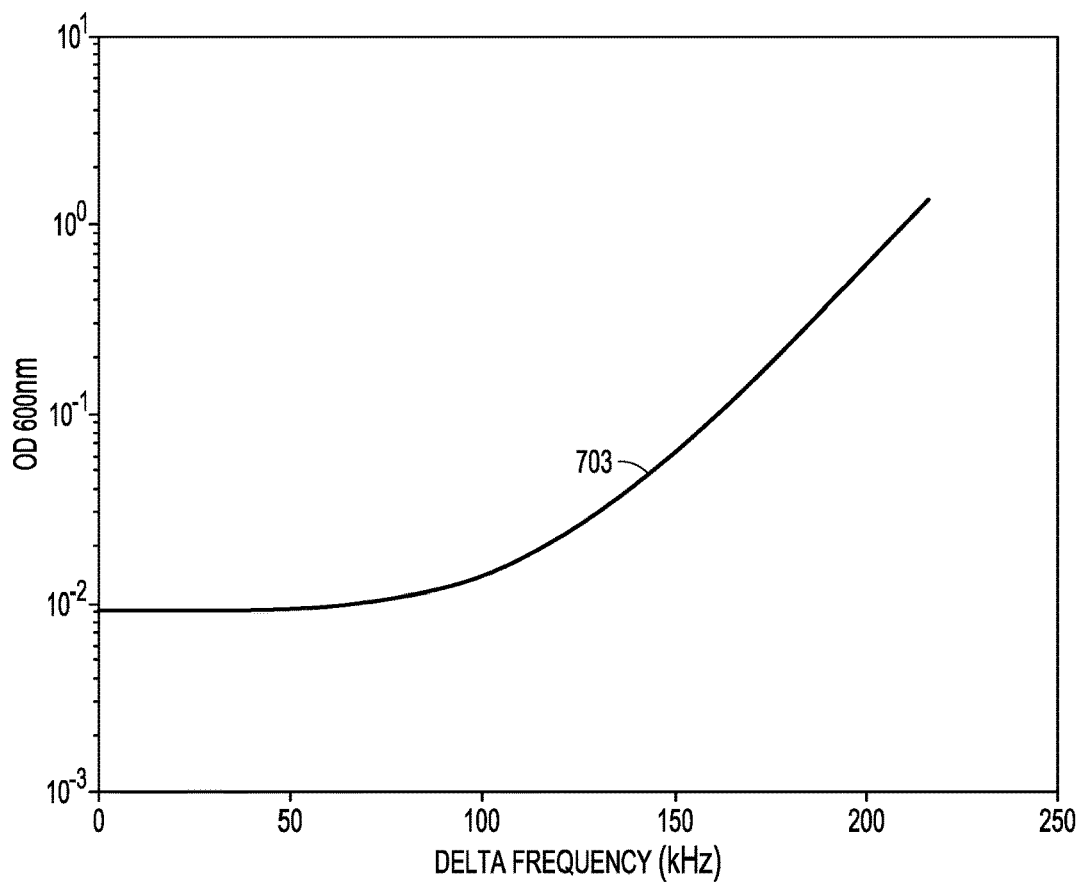
FIG. 7 illustrates a calibration curve made from model fits, showing relation of optical density measured at 600 nm to the change in resonant frequency, in accordance with various embodiments.

FIG. 6A shows data from FIG. 5 plotted as change in frequency vs. time. The response curve 603A is a first order response curve fit. The optical density measured at 600 nm is also plotted as a function of time and fit with a four parameter logistics curve 603B in FIG. 6B. The change in frequency (delta frequency) and the OD data can be fit with a first order and four parameter logistics model, respectively, as shown in FIGS. 6A-6B, such that a calibration curve 703 of OD vs. resonant frequency shift can be plotted such as in FIG. 7. FIG. 7 illustrates calibration curve 703 generated from model fits, showing relation of OD at 600 nm to the change in resonant frequency. Again, it is seen that the response is very sensitive at low cell concentrations. The geometric effects of the resonator on this calibration curve can be investigated.

To increase that amount of data of a system and method as taught herein, more real time culture tests can be run to correlate the on-line resonant frequency measurement to OD. A panel of controls can be run to ensure that the signal is coming from cell mass and not some other by-product of cell growth. Example of such tests can include a procedure to spin out the cells, return the media, and determine if the signal has returned to the starting level.

Figure 8:
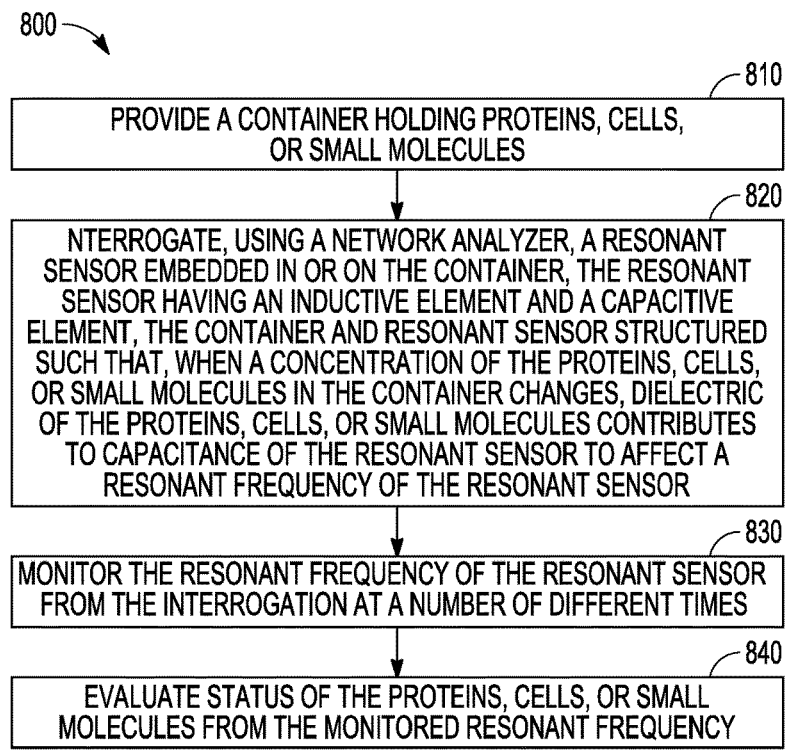
FIG. 8 is a flow diagram of features of an example method of wireless measurement of proteins, cells, or small molecules, in accordance with various embodiments.

FIG. 8 is a flow diagram of features of an embodiment of an example method 800 of wireless measurement of proteins, cells, or small molecules. At 810, a container holding proteins, cells, or small molecules is provided. At 820, using a network analyzer from outside the container, a resonant sensor embedded in or on the container is interrogated. The resonant sensor can have an inductive element and a capacitive element, where the container and resonant sensor can be structured such that, when a concentration of the proteins, cells, or small molecules in the container changes, dielectric permittivity and conductivity of the proteins, cells, or small molecules contributes to capacitance of the resonant sensor to affect a resonant frequency shift of the resonant sensor. The dielectric permittivity and conductivity can include sets of data where one of the dielectric permittivity and conductivity changes and the other one does not change. The sets of data can include data in which both the dielectric permittivity and the conductivity change. Interrogating the resonant sensor can include collecting scattering parameter data.

At 830, at a number of different times, the resonant frequency of the resonant sensor is monitored from the interrogation. At 840, status of the proteins, cells, or small molecules is evaluated from the monitored resonant frequency. Evaluating the status can include determining the resonant frequencies as a function of optical density.

Variations of method 800 or methods similar to method 800 can include a number of different embodiments that can be combined depending on the application of such methods and/or the architecture of systems in which such methods are implemented. Such methods can include transmitting data to a computer in response to interrogating the resonant sensor. Transmitting the data to the computer can include using Bluetooth protocol or other protocol. Variations of method 800 or methods similar to method 800 can include, in response to interrogating the resonant sensor, transmitting data to a computer via a network.

Variations of method 800 or methods similar to method 800 can include interrogating the resonant sensor periodically from a portable vector network analyzer and collecting data from the interrogation; transmitting the data to a computer; and determining resonant frequencies for each data point and smoothing the data with an averaging window. The resonant sensor can be interrogated every minute of a selected measurement period and the averaging window can be a ten minute averaging window. Other time periods can be used.

In various embodiments, an apparatus can comprise a container arranged to hold proteins, cells, or small molecules; and a resonant sensor embedded on the container. The resonant sensor can have an inductive element and a capacitive element, where the container and resonant sensor can be structured such that, when a concentration of the proteins, cells, or small molecules in the container changes, dielectric permittivity and conductivity of the proteins, cells, or small molecules contributes to capacitance of the resonant sensor to affect a resonant frequency shift of the resonant sensor. The apparatus can include a vector network analyzer to wirelessly receive signals from the resonant sensor to collect data reflecting resonant frequency of the resonant sensor over time. The container can include glass culture ware or plastic culture ware. The resonant sensor can be embedded in an inner surface of the container. The resonant sensor can include copper and polyimide with the copper epoxied side down in the container with the polyimide exposed to a medium in which the proteins, cells, or small molecules are disposed in the container. The resonant sensor can be etched from Pyralux. Other materials can be used for the container or resonant sensor.

In various embodiments, a system can comprise: a container arranged to hold proteins, cells, or small molecules, a resonant sensor, and a network analyzer. The resonant sensor can be embedded in or on the container, where the resonant sensor has an inductive element and a capacitive element, with the container and resonant sensor structured such that, when a concentration of the proteins, cells, or small molecules in the container changes, dielectric permittivity and conductivity of the proteins, cells, or small molecules contributes to capacitance of the resonant sensor to affect a resonant frequency shift of the resonant sensor. The network analyzer can be arranged to wirelessly interrogate the resonant sensor from outside the container and to transmit data collected wirelessly from the interrogation.

Variations of the system or similar systems can include a number of different embodiments that can be combined depending on the application of such systems and/or the architecture in which such systems are implemented. In such systems, the network analyzer can be arranged to wirelessly interrogate the resonant sensor to collect scattering parameter data. The network analyzer can be arranged to wirelessly transmit the collected data to a computer. The network analyzer can be arranged to wirelessly transmit the collected data to the computer via Bluetooth protocol or other protocol. The network analyzer can be arranged to wirelessly transmit the collected data to a communication interface. The communication interface can be arranged to transmit the data to a computer via a network. The network analyzer can be a portable vector network analyzer.

In various embodiments, a machine-readable storage device, such as computer-readable medium, can comprise instructions stored thereon, which, when performed by a machine, cause the machine to perform operations. The instructions can be executed by one or more processors associated with the machine. The operations can comprise: receiving data from a vector network analyzer, the data collected by the vector network analyzer from periodically interrogating a resonant sensor with the resonant sensor embedded in or on a container arranged to hold proteins, cells, or small molecules, with the vector network analyzer located outside the container; determining resonant frequencies for data collected at each collection time during the periodic interrogation; and evaluating status of the proteins, cells, or small molecules disposed in the container from determining the resonant frequencies. Changes in concentration of the proteins, cells, or small molecules in the container can change dielectric permittivity and conductivity of the proteins, cells, or small molecules, which contributes to capacitance of the resonant sensor to affect a resonant frequency shift of the resonant sensor. The data can be received in a system using the machine-readable storage device wirelessly from the vector network analyzer or via a wired connection to the vector network analyzer. The wired connection can be a network connection.

Variations of such a machine-readable storage device or similar machine-readable storage device can include a number of different embodiments that can be combined depending on the application of such storage devices and/or the architecture of systems in which such storage devices are implemented. Operations from executing instructions stored in such storage devices can include determining the resonant frequencies by smoothing the collected data with an averaging window. Relationships of resonant frequency, peak frequency, and changes in frequency with respect to time can be generated using the collected data. Relationships of resonant frequency, peak frequency, and changes in frequency with respect to optical density can be generated using the collected data. These relationships can be digitally stored in the storage devices or other storage devices such as but not limited to databases. These relationships can be provided as plots on a display device. From one or more of these relationships, the status of the proteins, cells, or small molecules disposed in the container can be determined. The determined status can include concentrations of the proteins, cells, or small molecules disposed in the container.

Figure 9A:
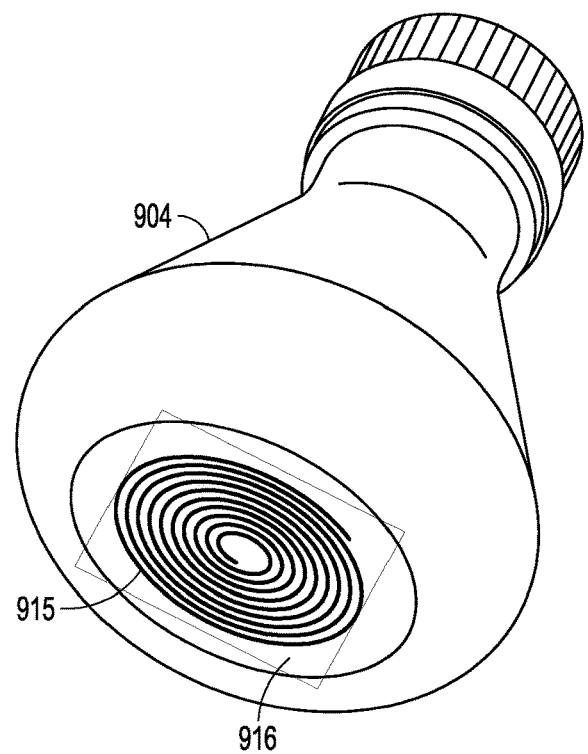
FIG. 9A illustrates an example sensor embedded on a container, in accordance with various embodiments.

FIG. 9A illustrates an embodiment of an example sensor embedded on a container. The arrangement of the sensor and the container shown in FIG. 9A is similar to that of FIG. 3, except the sensor is embedded on the outside of container 904, where container 904 holds fluid that can include proteins, cells, or small molecules being monitored. The sensor includes an electrically conducting coil 915 attached to an electrically insulating substrate 916. In this example, the sensor is an approximately 4 cm diameter sensor on the bottom of a culture vessel. Other sensor sizes can be used. The electrically conducting coil 915 can be a copper coil, though other materials may be used to construct the coil. The electrically insulating substrate 916 can be a polyimide substrate though other non-conducting materials can be used instead of or with polyimide. The sensor structured with electrically conducting coil 915 and insulating substrate 916 can be embedded on container 904 using epoxy or transfer tape used to adhere the sensor attached to the outside of container 904. The sensor can respond to a change in the complex permittivity of the liquid with container 904, where the liquid may experience a change in capacitance, such as with cell growth in the liquid, or the liquid may experience a change in the conductivity of the liquid, such as with a KCl solution. Such a sensor provides a resonator structure having an inductance provided by conducting coil 915 and a capacitance, which can be provided by contributions from insulating substrate 916, the epoxy, and contents of container 904.

Figure 9B:
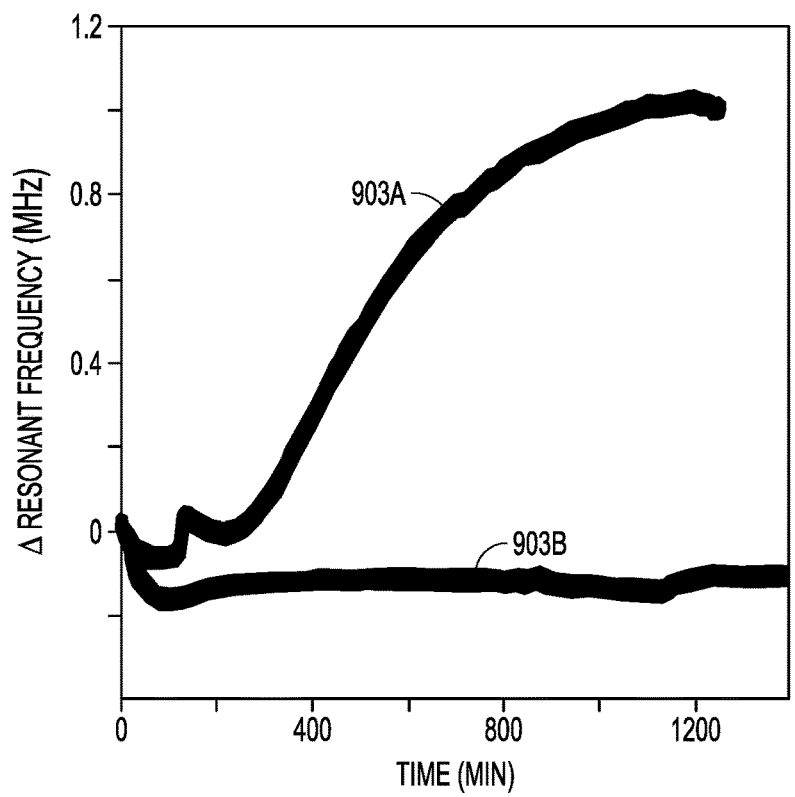
FIG. 9B shows plots of change of resonant frequency over time that can be measured using the sensor of FIG. 9A, in accordance with various embodiments.

FIG. 9B shows plots of change of resonant frequency over time that can be measured using the sensor of FIG. 9A. Plot 903A is a curve of a response of the sensor to 100 ml broth with *E. coli* in container 904. Plot 903B is a curve of a response of the sensor to broth with no *E. coli* in container 904, which can be used as control data.

Figure 10B:
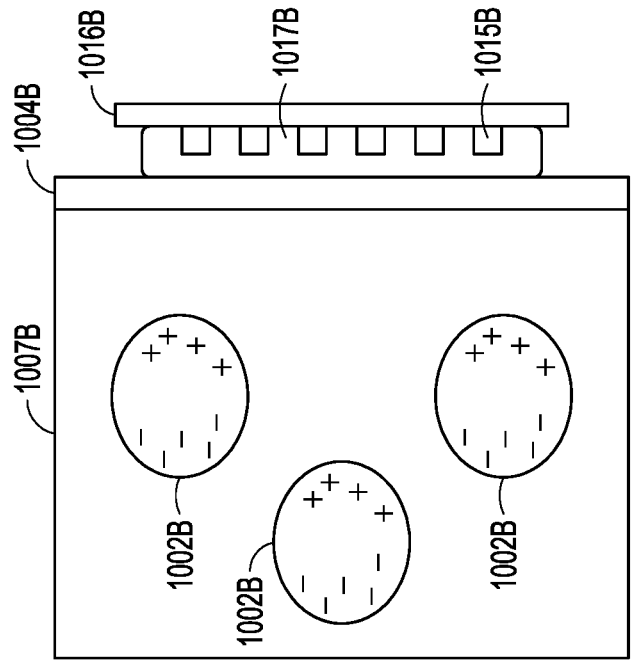
FIGS. 10A-10C illustrate schematics for various example methods of integration of a resonant sensor with a container, in accordance with various embodiments.
Figure 10A:
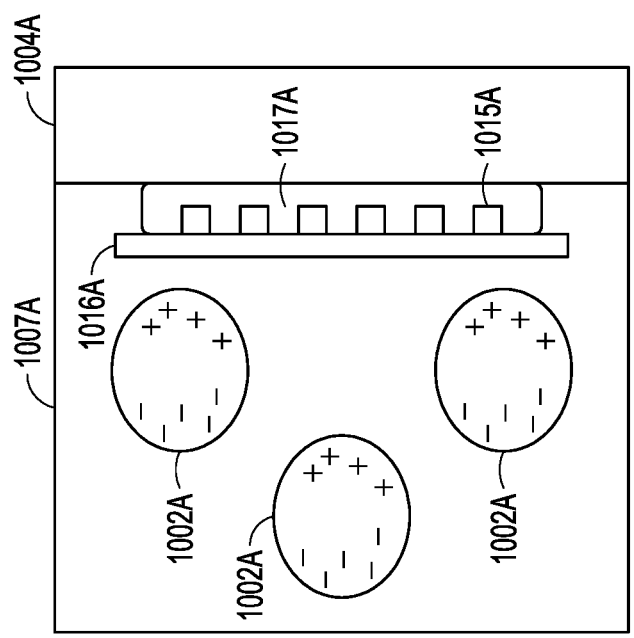
Figure 10C:
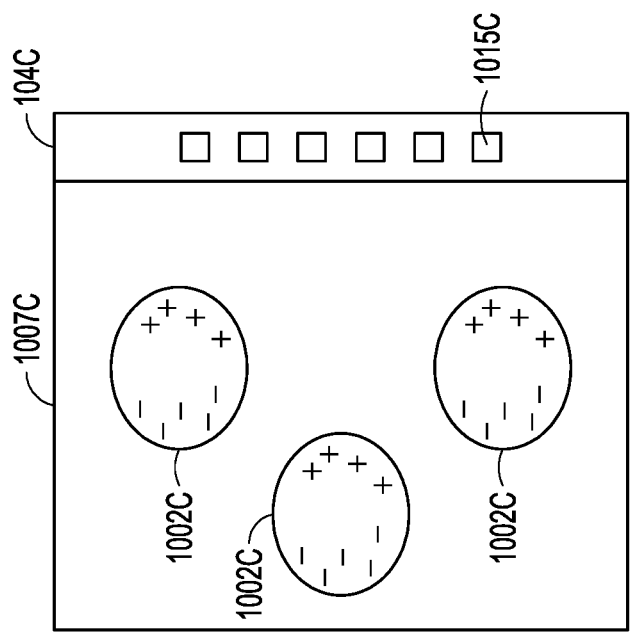

A resonant sensor can be embedded with or on a container by integrally attaching the sensor to an inside surface of the container, an outside surface of the container, or within the walls of the container. FIGS. 10A-10C illustrate schematics for embodiments of various example methods of integration of a resonant sensor with a container. FIG. 10A is a cross sectional view of a schematic of an embodiment of an example sensor inside a cell culture vessel. Cells 1002A are dispersed in fluid 1007A in the vessel having a portion 1004A of the vessel to which the sensor is embedded with the vessel. Only portion 1004A of the vessel is shown for ease of discussion. The vessel can be composed of non-conducting material. The sensor includes an electrically conducting coil 1015A attached to an electrically insulating substrate 1016A. The sensor is attached to an inner surface of portion 1004A of the vessel by an epoxy 1017A, which integrates electrically conducting coil 1015A with inner surface of portion 1004A. The electrically conducting coil 1015A can be a copper coil, though other materials may be used to construct the coil. The electrically insulating substrate 1016A can be a polyimide substrate though other non-conducting materials can be used instead of or with polyimide. Rather than an epoxy or other similar adhesive, a transfer tape can be used to adhere the sensor to the inner surface of portion 1004A. The sensor can respond to a change in the complex permittivity of the liquid 1007A within the vessel having portion 1004A, where the liquid may experience a change in capacitance, such as with cell growth in the liquid 1007A or the liquid may experience a change in the conductivity of the liquid 1007A.

FIG. 10B is a cross sectional view of a schematic of an embodiment of an example sensor embedded on a surface outside a cell culture vessel. Cells 1002B are dispersed in fluid 1007B in the vessel having a portion 1004B of the vessel to which the sensor is embedded with the vessel. The vessel can be composed of non-conducting material. Only portion 1004B of the vessel is shown for ease of discussion. The sensor includes an electrically conducting coil 1015B attached to an electrically insulating substrate 1016B. The sensor is attached to an outer surface of portion 1004B of the vessel by an epoxy 1017B, which integrates electrically conducting coil 1015B with outer surface of portion 1004B. The electrically conducting coil 1015B can be a copper coil, though other materials may be used to construct the coil. The electrically insulating substrate 1016B can be a polyimide substrate though other non-conducting materials can be used instead of or with polyimide. Rather than an epoxy or other similar adhesive, a transfer tape can be used to adhere the sensor to the outer surface of portion 1004B. The sensor can respond to a change in the complex permittivity of the liquid 1007B within the vessel having portion 1004B, where the liquid may experience a change in capacitance, such as with cell growth in the liquid 1007B or the liquid may experience a change in the conductivity of the liquid 1007B.

FIG. 10C is a cross sectional view of a schematic of an embodiment of an example sensor embedded within a wall of a cell culture vessel. Cells 1002C are dispersed in fluid 1007C in the vessel having a portion 1004C of the vessel to which the sensor is embedded within a wall of the vessel. The vessel can be composed of non-conducting material. Only portion 1004C of the vessel is shown for ease of discussion. The sensor includes an electrically conducting coil 1015C embedded within a wall of portion 1004C of the vessel. The electrically conducting coil 1015B can be a copper coil, though other materials may be used to construct the coil. The sensor can respond to a change in the complex permittivity of the liquid 1007C within the vessel having portion 1004C, where the liquid may experience a change in capacitance, such as with cell growth in the liquid 1007C or the liquid may experience a change in the conductivity of the liquid 1007C.

Figure 11A:
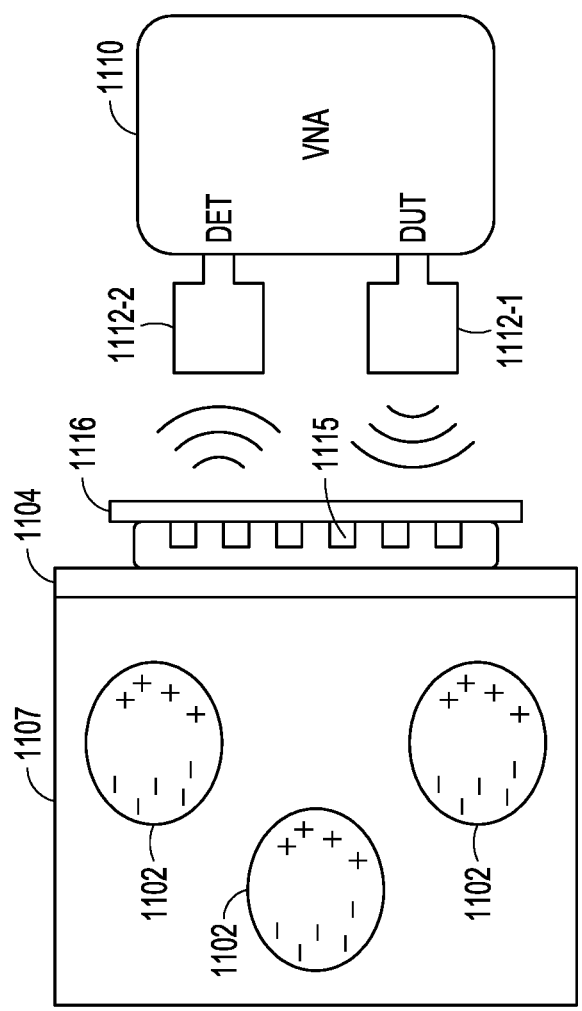
FIG. 11A is a schematic of an example sensor embedded on a surface outside a cell culture vessel interrogated by a vector network analyzer, in accordance with various embodiments.

FIG. 11A is a schematic of an embodiment of an example sensor embedded on a surface outside a cell culture vessel interrogated by a VNA 1110. Cells 1102 are dispersed in fluid 1107 in the vessel having a portion 1104 of the vessel to which the sensor is embedded with the vessel. The vessel can be composed of non-conducting material. Only portion 1104 of the vessel is shown for ease of discussion. The sensor includes an electrically conducting coil 1115 attached to an electrically insulating substrate 1116. The sensor is attached to an outer surface of portion 1104 of the vessel by an epoxy 1117, which integrates electrically conducting coil 1115B with outer surface of portion 1104. The electrically conducting coil 1115 can be a copper coil though other materials may be used to construct the coil. The electrically insulating substrate 1116 can be a polyimide substrate though other non-conducting materials can be used instead of or with polyimide. Rather than an epoxy or other similar adhesive, a transfer tape can be used to adhere the sensor to the outer surface of portion 1104. The sensor can respond to a change in the complex permittivity of the liquid 1107 within container 1104, where the liquid may experience a change in capacitance, such as with cell growth in the liquid 1107 or the liquid may experience a change in the conductivity of the liquid 1107. The sensor of FIG. 11A can be structured similar or identical to the sensor of FIG. 10B. Other sensor structures embedded in a container can be used with VNA 1110. However, the selection of materials and coil design of the sensor and the material and structure of the vessel of FIG. 11A may depend on the fluid and proteins, cells, or small molecules being monitored or the interrogating system.

The sensor embedded with portion 1104 of the container of FIG. 11A can be interrogated using VNA 1110. The interrogation can be implemented wirelessly. VNA 1110 can be arranged as a two loop vector network analyzer coupled to loop antenna 1112-1 and loop antenna 1112-2. Such an interrogation was discussed with respect to FIGS. 1 and 3. The amount of signal power (dB) transmitted and absorbed through the resonator sensor can be measured using VNA 1110. A network analyzer, like VNA 1110, operates by exciting the device under test (DUT) with a known power waveform and then measures (detects) the power that is reflected (in a one-port case) or transmitted (in a two-port case), where the arrangement in FIG. 11A is a two-port case. The output of VNA 1110 can be data providing the amount of power vs. waveform frequency (scattering parameters), which can be used to identify the resonant frequency. The output can be provided to a computer wirelessly, via a wired connection, or combination of wireless communication and wired communication. The wired connection can be part of a communication network, either a wide area network or a local area network. Arrangements, as taught herein, can be implemented using an interrogator that has no wire or electrode contact with the contents of the container being monitored. This approach allows for higher frequency interrogation, such as greater than 10 MHz, which also allows for smaller resonant circuit design.

Figure 11B:
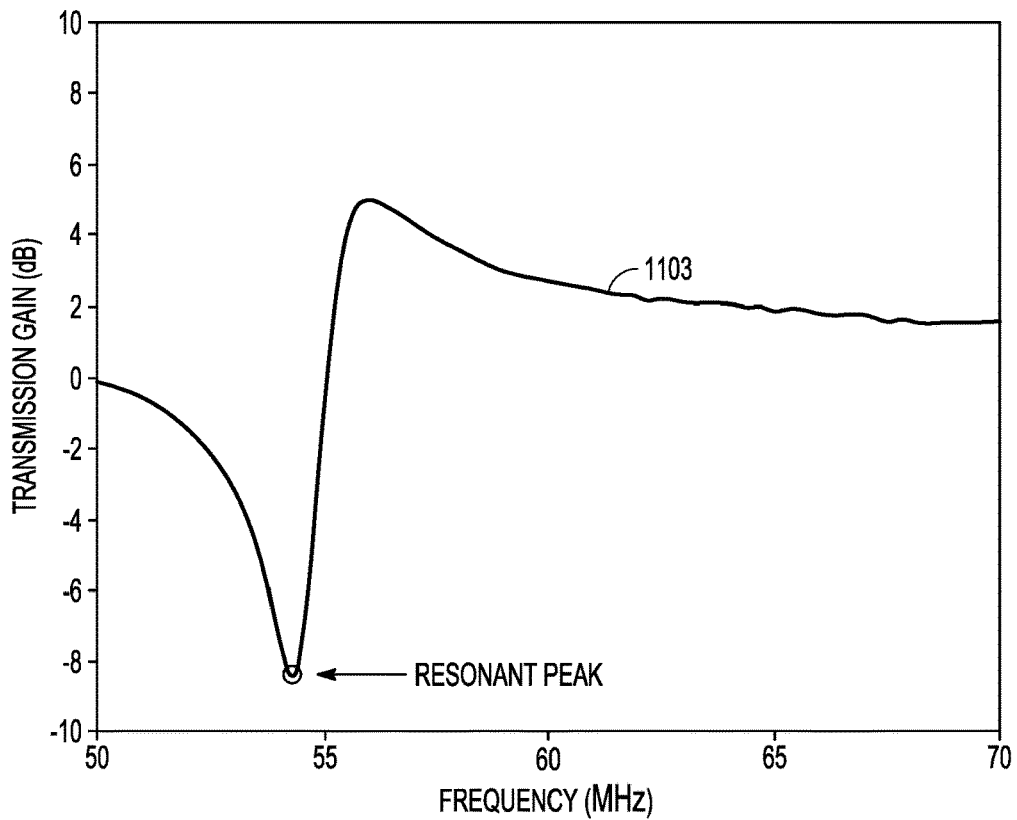
FIG. 11B shows a plot of transmission gain versus time, which can be generated from operating the arrangement of FIG. 11A, in accordance with various embodiments.

FIG. 11B shows a plot of transmission gain versus time, which can be generated from operating the arrangement of FIG. 11A. Curve 1103 can show the resonant peak from interrogating the sensor embedded with the container filled with liquid 1107 holding proteins, cells, or small molecules 1102.

Figure 12:
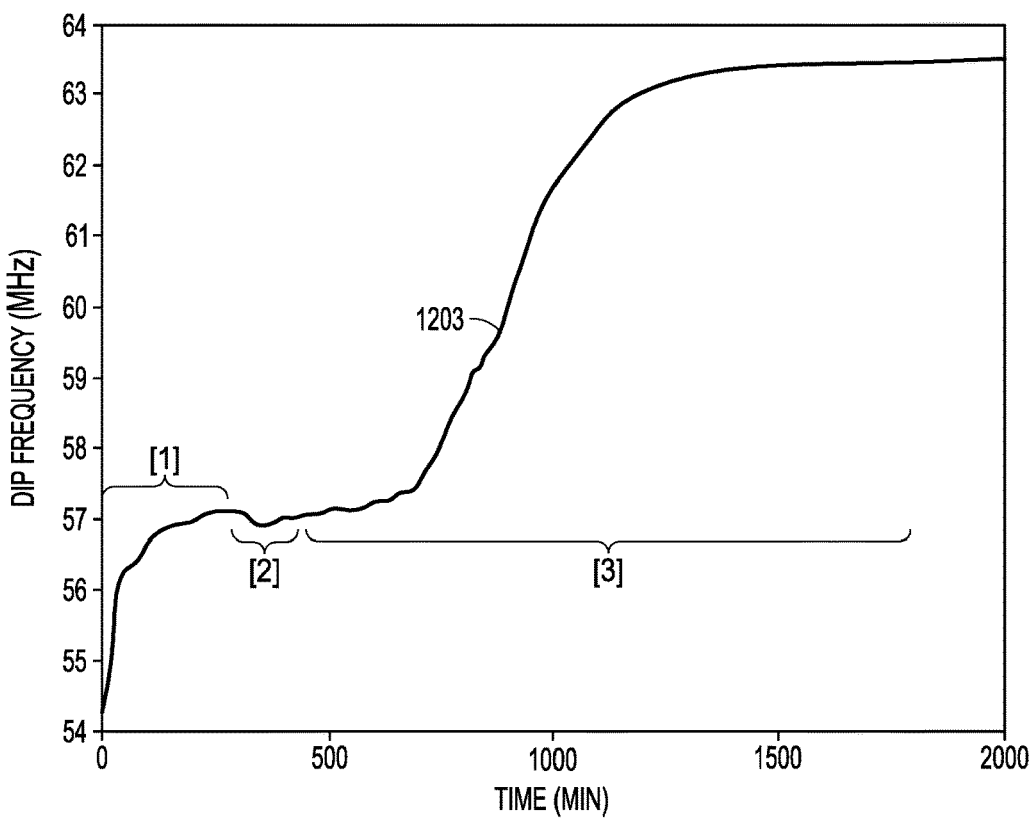
FIG. 12 shows a plot of resonant peak vs. time, in accordance with various embodiments.

FIG. 12 shows a plot of resonant peak vs. time. The plot in terms of dip frequency over time can be generated from an interrogation arrangement such as that shown with FIG. 11A. Three regions can be seen in curve 1203. Region 1 is for cooling of media having an initial transient. Region 2 corresponds to low concentration, suspended cell with a decrease in signal. Region 2 corresponds to high concentration, packing of cells in a sensor interrogation zone, which causes an increase in curve 1203.

Figure 13A:
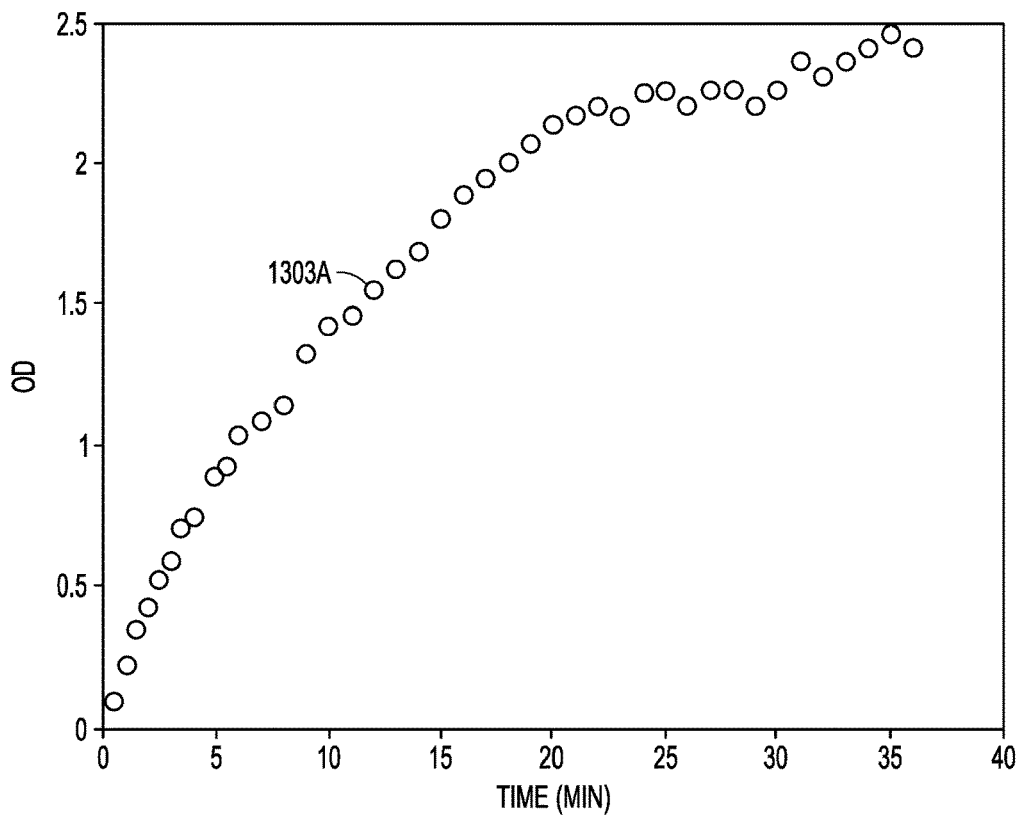
FIGS. 13A-13C show plots from measurements on a container filled with liquid holding proteins, cells, or small molecules that can be used for calibration correlated to optical density, in accordance with various embodiments.
Figure 13B:
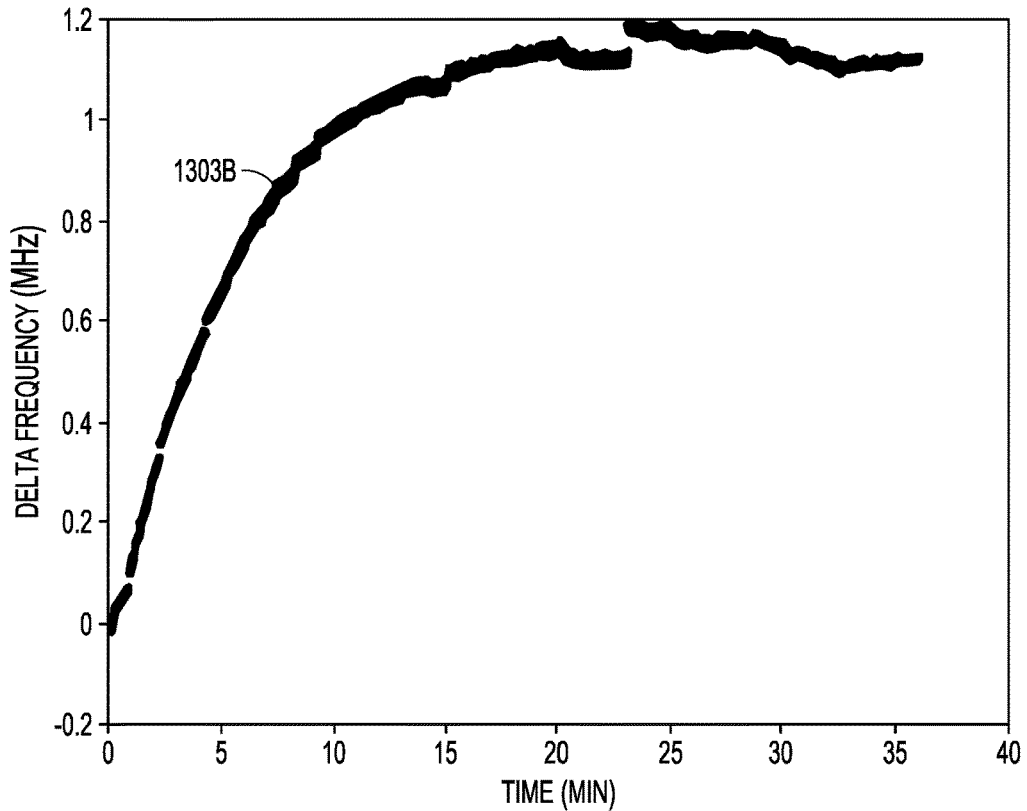
Figure 13C:
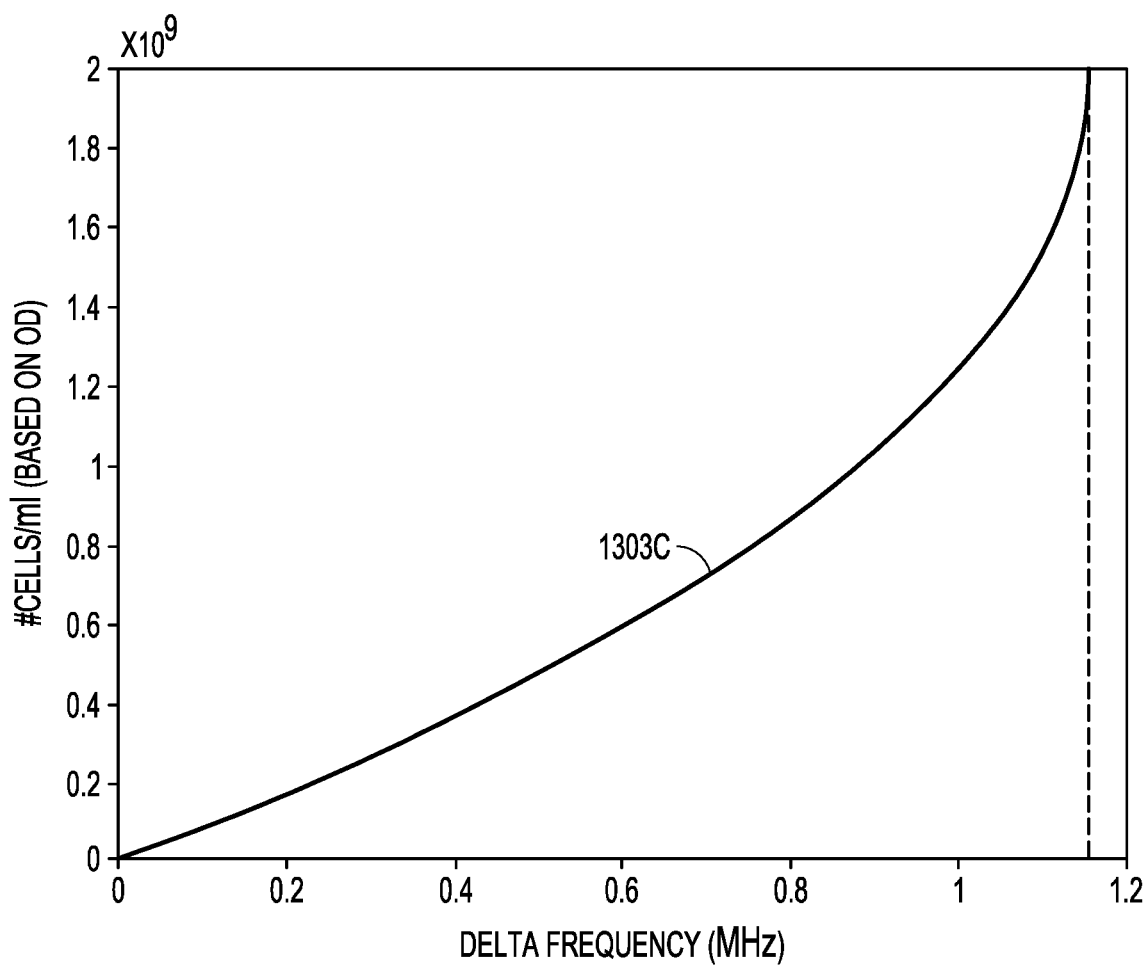

FIGS. 13A-13C show plots from measurements on a container filled with liquid holding proteins, cells, or small molecules that can be used for calibration correlated to optical density. FIG. 13A is a plot of optical density over time from optical density measurements on a subject container filled with liquid holding proteins, cells, or small molecules. FIG. 13B is a plot of delta frequency over time from resonant sensor interrogation measurements on the subject container. FIG. 13C is a plot of a number of cells per volume versus delta frequency, where the number of cells per volume is based on the optical density measured. Curve 1303C of FIG. 13C can be generated using curve 1303A of FIG. 13A and curve 1303B of FIG. 13B. Such plots will be cell type and reactor vessel dependent. From experiments, at lower densities and higher shake speeds of the subject container, there is a modest decrease in resonant frequency. However, further experiments can show that at slower shake speeds of the subject container and higher cell densities, a large increase in resonant frequency can result. Calibration curves can be generated for each application corresponding to container parameters, fluid in the respective container, and the proteins, cells, or small molecules monitored in the fluid.

The following are example embodiments of methods, apparatus, and systems, in accordance with the teachings herein.

An example apparatus 1 can comprise: a container arranged to hold proteins, cells, or small molecules; and a resonant sensor embedded in or on the container, the resonant sensor having an inductive element and a capacitive element, the container and resonant sensor structured such that, when a concentration of the proteins, cells, or small molecules in the container changes, dielectric permittivity and conductivity of the proteins, cells, or small molecules contributes to capacitance of the resonant sensor to affect a resonant frequency shift of the resonant sensor; and a vector network analyzer to wirelessly receive signals from the resonant sensor to collect data reflecting resonant frequency of the resonant sensor over time.

An example apparatus 2 can include elements of example apparatus 1, wherein the container includes a glass culture ware or a plastic culture ware.

An example apparatus 3 can include elements of any preceding example apparatus, wherein the resonant sensor is embedded in an inner surface of the container.

An example apparatus 4 can include elements of any preceding example apparatus, wherein the resonant sensor includes copper and polyimide with the copper epoxied copper side down in the container with the polyimide exposed to a medium in which the proteins, cells, or small molecules are in the container.

An example apparatus 5 can include elements of any preceding example apparatus, wherein the resonant sensor is etched from pryalux.

An example system 1 can comprise an apparatus of any of the preceding example apparatus.

An example system 2 can comprise: a container arranged to hold proteins, cells, or small molecules; a resonant sensor embedded in or on the container, the resonant sensor having an inductive element and a capacitive element, the container and resonant sensor structured such that, when a concentration of the proteins, cells, or small molecules in the container changes, dielectric permittivity and conductivity of the proteins, cells, or small molecules contributes to capacitance of the resonant sensor to affect a resonant frequency shift of the resonant sensor; and a network analyzer to wirelessly interrogate the resonant sensor from outside the container and to wirelessly transmit data collected from the interrogation.

An example system 3 can include elements of example system 2, wherein the network analyzer is arranged to wirelessly interrogate the resonant sensor to collect scattering parameter data.

An example system 4 can include elements of any preceding example systems, wherein the network analyzer is arranged to wirelessly transmit the collected data to a computer.

An example system 5 can include elements of any preceding example systems, wherein the network analyzer is arranged to wirelessly transmit the collected data to the computer via Bluetooth protocol.

An example system 6 can include elements of any preceding example systems, wherein the network analyzer is arranged to wirelessly transmit the collected data to a communication interface.

An example system 7 can include elements of any preceding example systems, wherein the communication interface is arranged to transmit the data to a computer via a network.

An example system 8 can include elements of any preceding example systems, wherein the network analyzer is a portable vector network analyzer.

An example method 1 can comprise operating any example apparatus 1-5.

An example method 2 can comprise forming any example apparatus 1-5.

An example method 3 can comprise operating any example system 1-8.

An example method 4 can comprise forming any example system 1-8.

An example method 5 can comprise: providing a container holding proteins, cells, or small molecules; interrogating, using a network analyzer outside the container, a resonant sensor embedded in or on the container, the resonant sensor having an inductive element and a capacitive element, the container and resonant sensor structured such that, when a concentration of the proteins, cells, or small molecules in the container changes, dielectric permittivity and conductivity of the proteins, cells, or small molecules contributes to capacitance of the resonant sensor to affect a resonant frequency shift of the resonant sensor; monitoring the resonant frequency of the resonant sensor from the interrogation at a number of different times; and evaluating status of the proteins, cells, or small molecules from the monitored resonant frequency.

An example method 6 can include elements of preceding example method 5, wherein evaluating the status includes determining the resonant frequencies as a function of optical density.

An example method 7 can include elements of any preceding example methods 5 and 6, wherein interrogating the resonant sensor includes collecting scattering parameter data.

An example method 8 can include elements of any preceding example methods 5-7, wherein the method includes transmitting data to a computer in response to interrogating the resonant sensor.

An example method 9 can include elements of any preceding example methods 5-8, wherein transmitting the data to the computer includes using Bluetooth protocol.

An example method 10 can include elements of any preceding example methods 5-9, wherein the method includes, in response to interrogating the resonant sensor, transmitting data to a computer via a network.

An example method 11 can include elements of any preceding example methods 5-10, wherein the method includes: interrogating the resonant sensor periodically from a portable vector network analyzer and collecting data from the interrogation; transmitting the data to a computer; and determining resonant frequencies for each data point and smoothing the data with an averaging window.

An example method 12 can include elements of any preceding example methods 5-11, wherein the resonant sensor is interrogated every minute of a selected measurement period and the averaging window is a ten minute averaging window.

An example machine-readable storage device comprising instructions, which, when executed by a set of processors, cause a system to perform operations, the operations comprising operations to perform elements of any of example methods 1-12.

An example method 13 can comprise: receiving data from a vector network analyzer, the data collected by the vector network analyzer from periodically interrogating a resonant sensor with the resonant sensor embedded in or on a container arranged to hold proteins, cells, or small molecules; determining resonant frequencies for data collected at each collection time during the periodic interrogation; and evaluating status of the proteins, cells, or small molecules disposed in the container from determining the resonant frequencies.

An example method 14 can include elements of preceding example method 13 and can include determining the resonant frequencies by smoothing the collected data with an averaging window.

An example method 15 can include elements of any preceding example methods 13 and 14 and can include generating relationships of resonant frequency, peak frequency, or changes in frequency with respect to time using the collected data.

An example method 16 can include elements of any preceding example methods 13-15 and can include generating relationships of resonant frequency, peak frequency, or changes in frequency with respect to optical density using the collected data.

An example method 17 can include elements of any preceding example methods 13-16 and can include digitally storing relationships generated using the collected data.

An example method 18 can include elements of any preceding example methods 13-17 and can include providing plots on displays of relationships generated using the collected data.

An example method 19 can include elements of any preceding example methods 13-18 and can include determining the status of the proteins, cells, or small molecules disposed in the container from relationships generated using the collected data.

An example method 20 can include elements of any preceding example methods 13-19 and can include determining the status of the proteins, cells, or small molecules disposed in the container to include determining concentrations of the proteins, cells, or small molecules disposed in the container.

An example machine-readable storage device 2 can comprise instructions, which, when executed by a set of processors, cause a system to perform operations, the operations comprising operations to perform elements of any of example methods 13-20.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description.

What is claimed is:

1. An apparatus comprising:
    a container arranged to hold proteins, cells, or small molecules;
    a resonant sensor embedded in or on the container, the resonant sensor having an inductive element and a capacitive element, the container and the resonant sensor structured such that, when a concentration of the proteins, cells, or small molecules in the container changes, dielectric permittivity and conductivity of the proteins, cells, or small molecules contributes to capacitance of the resonant sensor to affect a resonant frequency shift of the resonant sensor, the resonant sensor structured for contactless interrogation; and
    a vector network analyzer arranged to measure an amount of signal power transmitted or absorbed through the resonant sensor, as a function of frequency, with the vector network analyzer arranged to interrogate the resonant sensor with no wired connection to the resonant sensor and to wirelessly receive signals from the resonant sensor to collect data reflecting resonant frequency of the resonant sensor over time.

2. The apparatus of claim 1, wherein the container includes a glass culture ware or a plastic culture ware.

3. The apparatus of claim 1, wherein the resonant sensor is embedded in an inner surface of the container.

4. The apparatus of claim 1, wherein the resonant sensor includes copper and polyimide with the copper epoxied side down in the container with the polyimide exposed to a medium in which the proteins, cells, or small molecules are disposed in the container.

5. The apparatus of claim 1, wherein the resonant sensor is etched from Pyralux.

6. A system comprising:
a container arranged to hold proteins, cells, or small molecules;
a resonant sensor embedded in or on the container, the resonant sensor having an inductive element and a capacitive element, the container and the resonant sensor structured such that, when a concentration of the proteins, cells, or small molecules in the container changes, dielectric permittivity and conductivity of the proteins, cells, or small molecules contributes to capacitance of the resonant sensor to affect a resonant frequency shift of the resonant sensor, the resonant sensor structured for contactless interrogation with no wired connection to the resonant sensor; and
a network analyzer arranged to measure an amount of signal power transmitted or absorbed through the resonant sensor with the network analyzer arranged to wirelessly interrogate the resonant sensor from outside the container with no wired connection to the resonant sensor and to wirelessly transmit data collected from the interrogation.

7. The system of claim 6, wherein the network analyzer is arranged to wirelessly interrogate the resonant sensor to collect scattering parameter data.

8. The system of claim 6, wherein the network analyzer is arranged to wirelessly transmit the collected data to a computer.

9. The system of claim 8, wherein the network analyzer is arranged to wirelessly transmit, the collected data to the computer via Bluetooth protocol.

10. The system of claim 6, wherein the network analyzer is arranged to wirelessly transmit the collected data to a communication interface.

11. The system of claim 10, wherein the communication interface is arranged to transmit the data to a computer via a network.

12. The system of claim 6, wherein the network analyzer is a portable vector network analyzer.

13. A method comprising:
providing a container holding proteins, cells, or small molecules;
wirelessly interrogating, using a network analyzer outside the container, a resonant sensor embedded in or on the container to measure an amount of signal power transmitted or absorbed through the resonant sensor, the resonant sensor having an inductive element and a capacitive element, the container and resonant sensor structured such that, when a concentration the proteins, cells, or small molecules in the container changes, dielectric permittivity and conductivity of the proteins, cells, or small molecules contributes to capacitance of the resonant sensor to affect a resonant frequency shift of the resonant sensor, the resonant sensor structured for contactless interrogation with no wired connection to the resonant sensor;
monitoring the resonant, frequency of the resonant sensor from the interrogation at a number of different times; and
evaluating status of the proteins, cells, or small molecules from the monitored resonant frequency.

14. The method of claim 13, wherein evaluating the status includes determining the resonant frequencies as a function of optical density.

15. The method of claim 13, wherein interrogating the resonant sensor includes collecting scattering parameter data.

16. The method of claim 13, wherein the method incudes to transmitting data to a computer in response to interrogating the resonant sensor.

17. The method of claim 16, wherein transmitting the data to the computer includes using Bluetooth protocol.

18. The method of claim 13, wherein the method includes, in response to interrogating the resonant sensor, transmitting data to a computer via a network.

19. The method of claim 13, wherein the method includes:
interrogating the resonant sensor periodically from a portable vector network analyzer and collecting data from the interrogation;
transmitting the data to a computer; and
determining resonant frequencies for each data point and smoothing the data with an averaging window.

20. The method of claim 19, where the resonant sensor is interrogated every minute of a selected measurement period and the averaging window is a ten minute averaging window.

21. The apparatus of claim 1, wherein the apparatus includes one or more processors arranged to execute stored instructions to evaluate, from the data collected by the vector network analyzer, status of the proteins, cells, or small molecules from one or more changes in the resonant frequency of the resonant sensor.

22. The method of claim 13, wherein the method includes interrogating the resonant sensor at an interrogation frequency equal to or greater than 10 MHz.

* * * * *

UNITED STATES PATENT AND TRADEMARK OFFICE
CERTIFICATE OF CORRECTION

PATENT NO. : 11,105,761 B2
APPLICATION NO. : 16/793617
DATED : August 31, 2021
INVENTOR(S) : Reuel et al.

It is certified that error appears in the above-identified patent and that said Letters Patent is hereby corrected as shown below:

In the Drawings

Sheet 5 of 11, Fig. 8, reference numeral 820, Line 1, delete "NTERROGATE," and insert --INTERROGATE,-- therefor Sheet 8 of 11, Fig. 10C, reference numeral 104C, delete "104C" and insert --1004C-- therefor In the Specification In Column 2, Line 22, after "logical", insert --,--

In Column 2, Line 47, delete "Berger." and insert --Berger,-- therefor

In Column 3, Line 65, delete "305." and insert --304.-- therefor

In Column 8, Line 37, delete "1115B" and insert --1115-- therefor

In Column 8, Line 38, after "coil", insert --,--

In the Claims

In Column 13, Line 34, in Claim 9, delete "transmit," and insert --transmit-- therefor In Column 14, Line 3, in Claim 13, after "concentration", insert --of--

In Column 14, Line 11, in Claim 13, delete "resonant," and insert --resonant-- therefor In Column 14, Lines 22-23, in Claim 16, delete "incudes to" and insert --includes-- therefor Signed and Sealed this
Eleventh Day of January, 2022

Drew Hirshfeld
*Performing the Functions and Duties of the
Under Secretary of Commerce for Intellectual Property and
Director of the United States Patent and Trademark Office*